(12) United States Patent
Kaplan et al.

(10) Patent No.: US 7,134,460 B2
(45) Date of Patent: Nov. 14, 2006

(54) METHOD AND APPARATUS FOR PLACING TABLETS INTO POCKETS OF THERMOFORMED BOTTOM FOIL

(75) Inventors: Horst Kaplan, Oerlinghausen (DE); Heinrich Barke, Lage (DE)

(73) Assignee: MediSeal GmbH, Schlose-Holt Stukenbrock (DE)

( * ) Notice: Subject to any disclaimer, the term of this patent is extended or adjusted under 35 U.S.C. 154(b) by 0 days.

(21) Appl. No.: 11/247,390

(22) Filed: Oct. 11, 2005

(65) Prior Publication Data

US 2006/0076077 A1  Apr. 13, 2006

(30) Foreign Application Priority Data

Oct. 12, 2004 (DE) .............. 10 2004 049 560

(51) Int. Cl.
*B65B 1/04* (2006.01)
(52) U.S. Cl. .............. 141/200; 141/2; 141/18
(58) Field of Classification Search ............ 141/2, 141/18, 98, 67, 200, 234; 221/241, 296, 221/186, 298, 289, 25, 26, 131; 53/246, 53/505
See application file for complete search history.

(56) References Cited

U.S. PATENT DOCUMENTS

| | | | |
|---|---|---|---|
| 2,983,374 A | 5/1961 | Engleson et al. | |
| 4,627,225 A | 12/1986 | Faller et al. | |
| 5,596,865 A | 1/1997 | Kramer | |
| 5,802,804 A | 9/1998 | Esposti et al. | |
| 5,845,810 A * | 12/1998 | Laznicka | 221/172 |
| 6,311,462 B1 | 11/2001 | Amborn et al. | |
| 6,439,426 B1 * | 8/2002 | Baroncini | 221/241 |
| 2001/0017025 A1 | 8/2001 | Amborn et al. | |

FOREIGN PATENT DOCUMENTS

| | | |
|---|---|---|
| CH | 291072 | 9/1953 |
| CH | 489 392 | 4/1970 |
| CH | 602 421 | 12/1977 |
| DE | 866 476 | 2/1953 |
| DE | 2 239 344 | 2/1974 |
| DE | 35 41 672 | 11/1985 |
| DE | 44 06 089 | 2/1994 |
| DE | 100 26 331 | 2/2002 |
| EP | 1 251 073 | 10/2002 |

\* cited by examiner

*Primary Examiner*—Steven O. Douglas
(74) *Attorney, Agent, or Firm*—Thomas, Kayden, Horstemeyer & Risley

(57) ABSTRACT

A method and an apparatus (1) serve to place tablets (2) into pockets (3) of thermoformed bottom foil (4). The tablets (2) are accumulated as they are located in their flat position. The tablets (2) are rotated in an erecting station (9) such that they reach an approximately upright position. A plurality of lines of approximately upright tablets (2) is formed. The approximately upright tablets (2) are rotated back into their flat position by a transfer unit (24) including a plurality of channels (28). The tablets (2) are then placed into the pockets (3) of the bottom foil (4) by the transfer unit (24).

23 Claims, 13 Drawing Sheets

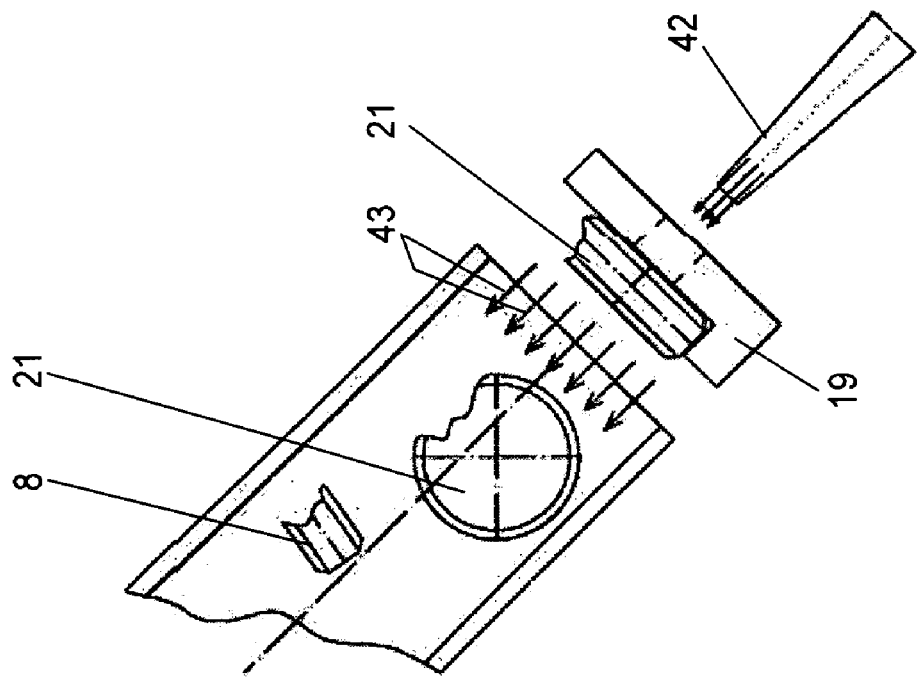
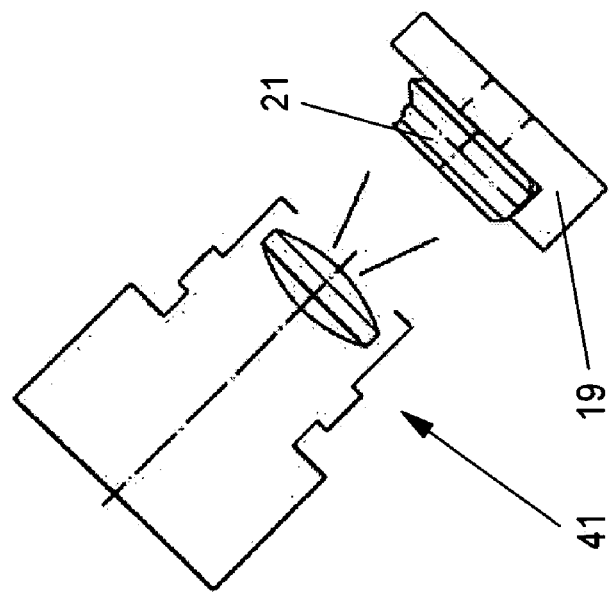
Fig. 7

METHOD AND APPARATUS FOR PLACING TABLETS INTO POCKETS OF THERMOFORMED BOTTOM FOIL

CROSS REFERENCE TO RELATED APPLICATIONS

This application claims priority to co-pending German Patent Application No. DE 10 2004 049 560.2 entitled "Verfahren und Vorrichtung zum Einlegen von Tabletten in die Höfe tiefgezogener Bodenfolie", filed Oct. 12, 2004.

FIELD OF THE INVENTION

The present invention generally relates to a method of packaging tablets by placing tablets into pockets of thermoformed bottom foil. More particularly, the present invention relates to such a method in which each tablet is separately introduced into a pocket of the bottom foil after having removed pieces and dust caused by damaged tablets. The present invention also relates to an apparatus for placing tablets into pockets of thermoformed bottom foil.

BACKGROUND OF THE INVENTION

A method and an apparatus for placing tablets into pockets of thermoformed bottom foil are known from U.S. Pat. No. 6,311,462 B2. The tablets are produced by pressing them in a tablet press in a quick way. A great numbers of tablets reach an upwardly declined slide. In the following, the tablets located in their flat position are received on a conveying belt. Side walls having a special design are arranged above the conveying belt to store the tablets. Storing of the tablets also serves to distribute the tablets in a direction transverse to the working direction in front of a line forming element in which the tablets are arranged as lines of tablets, meaning such that the tablets are arranged one after the other in a line in a way that two adjacent flat tablets only contact one another at one location of their edges. For this purpose, the line forming element includes channels in which the lines of tablets are stored. The exit of the line forming element is closed by a stop bar such that the tablets are stored in the line forming element. A transfer unit includes sucking elements. The transfer unit is lowered from above the lines of tablets (which are located in the line forming element) such that the foremost tablets which are retained by the stop bar are received in their flat position by sucking, and they are moved in the direction of the bottom foil and separately placed into a pocket located in the bottom foil. The sucking elements of the transfer unit also engage damaged tablets in case these are comparatively big. Smaller pieces of tablets cannot be received by the sucking elements. Thus, not only undamaged tablets, but also damaged tablets are placed into the pockets located in the bottom foil, and there are empty pockets containing no tablet at all. The stop bar is designed to be moved in an upward direction such that dust and smaller broken tablet pieces located in the line forming element can be removed. As soon as new tablets in the line forming element have followed, the stop bar has to be relocated into its effective position. It is also possible to manually open the stop bar to commonly remove tablet pieces and undamaged tablets as trash for a controllable period of time, and to thus clean portions of the line forming element. It is to be understood that the working velocities of the separate stations are coordinated in a way that there are as few as possible empty pockets.

A drawback of the known method and apparatus is the fact that the stress acting upon the tablets on their from the tablet press into the pockets of the bottom foil is comparatively great such that there is a respectively great proportion of broken pieces and dust, especially when processing tablets which are comparatively soft. Broken pieces and dust result in operation failures which have to be remedied, one the one hand, and in incorrect packages including pockets containing partly broken tablets and/or no tablets. This operation cannot be prevented although sucking off units are arranged at different locations, the sucking off units serving to suck off tablet dust and smaller broken tablet pieces.

SUMMARY OF THE INVENTION

The present invention relates to a method of placing tablets into pockets of thermoformed bottom foil, the tablets having two faces and a rim portion. The method includes the steps of: accumulating the tablets as they are located in their flat position in which the tablets are supported on one of the faces; rotating the tablets such that they reach an approximately upright position in which the tablets are at least partly supported on the rim portion; forming a plurality of lines of approximately upright tablets; rotating the approximately upright tablets back into their flat position; and placing the tablets into the pockets of the bottom foil as the tablets are located in their flat position.

The present invention also relates an apparatus for placing tablets into pockets of a thermoformed bottom foil, the tablets having two faces and a rim portion. The apparatus includes an erecting station, the erecting station being designed and arranged to rotate the tablets from a flat position in which the tablets are supported on one of the faces into an approximately upright position in which the tablets are at least partly supported on the rim portion. The apparatus further includes a transfer unit, the transfer unit including a plurality of channels, the channels being designed and arranged to rotate the tablets from the approximately upright position back into the flat position, the transfer unit being designed and arranged to place the tablets into the pockets of the bottom foil as the tablets are located in their flat position.

The tablets (pellets) treated by the novel method and processed on the novel apparatus are disc-like bodies substantially having a cylindrical edge portion and two circular surfaces which may be plain, concave, convex or differently shaped. The tablets or pellets may be such ones from the pharmacy field, but also such ones from the field of candy production and the like. Preferably, the tablets are designed as disc-like bodies having a diameter to thickness ratio of approximately 3:1. Thus, especially thin tablets may be processed and tablets which have not been pressed to be extremely compressed. Consequently, when treating the tablets until the point of packaging, there is a substantial danger of the tablets breaking. For example, such tablets are known as fizzy tablets or effervescent tablets. For such fragile tablets, there is not only the danger of breakage in the form of pieces occurring along the path of movement of the tablets between the tablet press and packaging, but there also result comparatively great amounts of dust due to friction and handling of the tablets. Similar to the pieces and in addition to the pieces, such dust leads to the danger of clogging and consequently to interruptions of operation in combination with the requirement of cleaning.

With the novel method and apparatus for placing tablets into pockets of thermoformed bottom foil, it is possible to carefully treat and process tablets such that the danger of breakage is reduced. Undamaged tablets are placed into the thermoformed pockets of a bottom foil at increased operational safety.

The present invention is based on the concept of rotating (turning) the tablets from their flat position into an upright position to further process the tablets in their upright position. The rotated upright position is maintained during a substantial portion of the process. Just before the step of placing the tablets into the pockets of the thermoformed bottom foil, the tablets are rotated back from their upright position into their flat position.

The flat position is to be understood as the position in which the axis of the tablet is arranged to be perpendicular or at least approximately perpendicular to the surface on which the tablet is supported, for example when the tablet slides down on a declined slide. The axis of the tablet is to be understood as the axis of symmetry which is perpendicular to the top and bottom side of the tablet. The rotated upright position is to be understood as a position in which the axis of the tablet is approximately parallel to the surface on which the tablet is supported or in which the tablet is oriented at a comparatively small angle thereto. In the first case in which the tablet is arranged such that its axis is parallel or horizontal, the tablet is supported on its edge (or rim). In the other case, meaning when the tablet is oriented in a slightly inclined direction, there are forces partly engaging the edge or rim of the tablet and partly engaging the two faces (meaning the front side and the bottom side) of the tablet. In the later case, a distribution of the forces and thus a distribution of the stress acting upon the tablet are realized when handling the tablet. Consequently, the danger of breakage is reduced. Since the tablets have an edge or a rim which is designed as an arc of a circle, there is the possibility of further moving the tablets in their upright position by rolling them on the edge or the rim. In other words, the sliding friction occurring during movement of the tablets in their flat position is replaced by rolling friction occurring during rolling of the tablets. Thus, the stress acting upon the tablets is reduced. The edge or the rim of the tablet is better suitable for accepting forces than the two faces of the tablets. The danger of breakage is substantially reduced by treatment of the tablets in the rotated upright position. This is a surprising advantageous effect of the present invention since tablets are pressed in a tablet press in a direction perpendicular to their plane of main extension.

When the tablets are rotated from their flat position by about 90° to reach their upright position, they are supported on their edge such that rolling friction is fully used during their transportation. There may be comparatively low sliding frictional forces acting upon the faces of the tablets being caused by guiding elements, guiding bars and the like.

However, it is also possible to rotate the tablets from their flat position only by approximately 45° to 60°, for example, into their rotated position, and to realize a distribution of the forces in this way. All these rotated positions are suitable to carefully treat the tablets. Especially, there is the possibility of individualizing the tablets in their rotated position to then check the tablets separately with respect to damages.

The upright tablets of the lines of tablets are individualized, and they are checked with respect to damages in their individualized condition. Damaged tablets are separately removed such that in the following only undamaged tablets are further processed. The danger of such undamaged tablets being damaged during following method steps is comparatively low. There only are few following method steps and the tablets have already been stressed to a comparatively great extent in preceding method steps. Thus, in case the respective tablet had been sensitive to breakage, it would have broken before.

The undamaged checked tablets of the lines of tablets are accumulated with a surplus in their individualized condition. This means that there are a greater number of tablets in the lines of tablets compared to the number of pockets located in the line of pockets in the bottom foil. During this accumulation, it is also possible to change the distance between two adjacent lines of tablets to correspond to the distance between the pockets in the bottom foil. The tablets are placed in a plate-like transfer unit in their individualized rotated position, the tablets being supported with their edges on a bottom. The transfer unit may also be called a transfer shuttle. The rotational movement of the tablets back into the flat position is realized during passage of the tablets through the transfer unit and thus directly before placing the tablets into the pockets. The erecting movement of the tablets from the flat position into the rotated position had been realized early in the process, preferably directly after the tablets having exited from a tablet press or from a reservoir. Many important method steps are realized in the upright position of the tablets.

The erecting station of the novel apparatus may include a plurality or a majority of lamellas being designed and arranged such that gaps are formed between the lamellas. The lamellas substantially extend in a vertical direction, and they are designed and arranged to move in a vertical direction. The gaps are designed to be closed towards the bottom side. This may be realized by separate plates or by a bottom continuously extending over the working width. The erecting station includes passages having dimensions corresponding to the thickness and the diameter of the tablets. The dimensions are chosen such that one tablet can pass through a passage at a time by rolling. Simultaneous passage of a plurality of tablets through one passage and wedging up of the tablets is prevented. The working planes of the tablets are arranged to be transverse such that the accumulated tablets are brought into their upright position, meaning they are rotated about a certain extent. The lamellas may be arranged as two packets of lamellas. One of the packets of lamellas is stationary and the other packet of lamellas is arranged to be movable with respect to the first packet of lamellas. In this way, one attains inclined surfaces at which the tablets can slide into the gaps between the lamellas which results in rotation of the tablets such that they attain their upright position. However, it is also possible to move both packets of lamellas with respect to one another or not to design the lamellas to be uniformly moved, but instead to move the lamellas in a series over the working width in a transverse direction. The lamellas may be arranged to be pivotable about a common axis. There are a number of possibilities of moving the lamellas with a vertical component of movement. For example, a crank mechanism or a cam mechanism may be used. The erecting station may also include a vibration drive which superimposes the up and down movement of the lamellas. The erecting station may also be designed as a storing or accumulating station. Usually, it is directly arranged downstream of the exit of a tablet press to allow for substantial treatment of the tablets occurring in their upright position.

In an especially preferred exemplary embodiment of the novel apparatus, the transfer unit includes two plates being placed upon one another. The plates substantially extend in a horizontal direction. The plates are designed and arranged to be commonly movable, especially to be moved from a loading position into a delivery position above the bottom foil. On the other hand, the two plates are designed and arranged to be movable with respect to one another. The upper plate includes impressions or openings for placement of the tablets, the impressions extending through the entire upper plate in a vertical direction. The impressions preferably have a rectangular cross-section corresponding to the diameter and the thickness of the tablets. It is to be understood that the clearance required for the movement of the tablets is also taken into account. The two plates are designed and arranged to be movable with respect to one another to reach a position in which the bottom plate closes the impressions of the upper plate. In this position, the tablets are placed into the impressions. Preferably, the impressions are already located in an arrangement corresponding to the arrangement of the pockets in the bottom foil such that it is not necessary to change the arrangement of the tablets during transfer. The bottom plate includes channels being inclined, bent or arcuate shaped. The tablets can slide through the channels with a clearance such that they are moved from the upright position back into the flat position. Relative positioning of the top and bottom plate with respect to one another makes it possible to connect the channels of the bottom plate to the impressions of the top plate. In this connecting position, the tablets slide into the pockets of the bottom foil while rotating back into their flat position as described above. This plate-like design of the transfer unit makes it possible to deliver the tablets just above the bottom foil, meaning at a comparatively small height of fall such that the danger of breakage is also substantially reduced during this step of treatment. The transfer unit may be designed as a form element and in a way to be easily replaceable in case a different arrangement of the tablets in the bottom foil is to be used and/or tablets of a different size are to be packed.

It makes sense to arrange a storing and delivery station between the erecting station and the transfer unit. The storing and delivery station is designed and arranged to store or accumulate the lines of tablets with a surplus of tablets and to deliver the tablets with a surplus of tablets in an individualized manner into the impressions of the transfer unit of a number of tablets corresponding to the arrangement of the pockets in the bottom foil. In this way, there is the possibility of coordinating the stations of the apparatus in a controlled way with respect to one another. This especially applies when the tablets are checked with respect to their undamaged state and when damaged tablets are to be singled out. The use of a surplus of tablets in the storing and delivery station ensures that all impressions of the transfer unit are filled such that there are no empty pockets in the packages.

Furthermore, there may be a control station being designed and arranged to check the individualized tablets with respect to damages and to cause removal of damaged tablets. Such a control station preferably operates with cameras which especially check the edges of the tablets in a top view. The tablets may be conveyed in the control station at slightly inclined orientation. Preferably, each single tablet is checked in a clocked manner when the tablet is individualized and not moving. Due to the inclined position of the tablets at this place, it is possible to arrange and use a majority of cameras and ejecting units at a small space.

The erecting station may include a unit for sucking off dust and pieces of tablets from in between the lamellas. It also makes sense to arrange passage gaps for pieces and dust. When removing damaged tablets, dust and pieces of tablets are also removed, for example by sucking them off or blowing them off such that only undamaged tablets are fed into the storing and delivery station. A unit for sucking off dust and pieces of tablets from the impressions and from the channels may also be associated with the transfer unit such that it is possible to continuously clean the transfer unit.

The novel apparatus includes a plurality of stations being arranged one after the other in the flow of material. Directly downstream of the tablet press, the tablets are guided on a slide or on a declined plane as the tablets are located in their flat position. The declined plane may include openings such that pieces of tablets the dimensions of which are smaller than the diameter of the openings in each direction can fall through the openings in the slide. Thus, bigger tablets only having less substantial damages at the edge portions remain in the flow of tablets. The flow of tablets being unsorted and being located in their flat position then enters the erecting station including a plurality of lamellas. The lamellas are not only designed and arranged to extend in the conveying direction, especially in a downwardly declined way, but also to include protrusions protruding in a perpendicular direction. These protrusions form some sort of a weir and thus collect the tablets. There are openings in the transition region of these lamellas. These openings are slightly greater than the thickness and the diameter of a tablet. The tablets are brought into their upright position in the erecting station, and they are moved on by rolling, the tablets moving through the openings. Again, dust and smaller pieces of tablets are removed. The tablets then reach the exit of the erecting station in the form of lines of tablets. The tablets enter a control station, the tablets being simultaneously individualized. This means that the tablets get free from contact to adjacent tablets such that they are spaced apart from one another and such that they can be controlled with respect to damages in a simple way, for example by an optical system. The control station may include a cam belt or a different endless belt being suitable to receive the tablets in a spaced apart manner and such that they are freely visible. By means of a respective control apparatus, damaged tablets can be blown and/or sucked away, the tablets being simultaneously removed from the product flow. In this way, only proper undamaged tablets are delivered to a collecting and delivery station by the control station. Once again, the tablets are guided and treated in their rotated position in the collecting and delivery station. The tablets are collected in an amount which is more than the number of tablets corresponding to the arrangement of the pockets to prevent empty pockets. A movable stop element and the like is arranged at the end of the collecting and delivery station. The stop element is designed to be moved to alternately reach two positions. In the first position, delivery of tablets is prevented. In the second position, tablets can be delivered into the impressions being located in the transfer unit in a controlled way by the collecting and delivery station. As long as the transfer unit is located outside of the region of the collecting and delivery station, further delivery of tablets is prevented. The transfer unit places an entire array of tablets into the pockets of the bottom foil within one single stroke. The tablets are simultaneously placed into the pockets in a way corresponding to the arrangement of the pockets. This is realized by a relative movement of the two plates of the transfer unit with respect to one another such that the channels being located in the bottom plate are connected to the impressions being located in the top plate. In this position, the backward stroke of the transfer unit from the bottom foil below the collecting and delivery station can take place. Simultaneously, a sucking apparatus serves to suck off dust and pieces of tablets possibly being located within the impressions or channels. Then, the next packaging step takes place in the known way by connecting a top foil on the bottom foil being filled with tablets.

Other features and advantages of the present invention will become apparent to one with skill in the art upon examination of the following drawings and the detailed description. It is intended that all such additional features and advantages be included herein within the scope of the present invention, as defined by the claims.

BRIEF DESCRIPTION OF THE DRAWINGS

The invention can be better understood with reference to the following drawings. The components in the drawings are not necessarily to scale, emphasis instead being placed upon clearly illustrating the principles of the present invention. In the drawings, like reference numerals designate corresponding parts throughout the several views.

FIG. 7 is a view of a control station.

DETAILED DESCRIPTION

Figure 1:
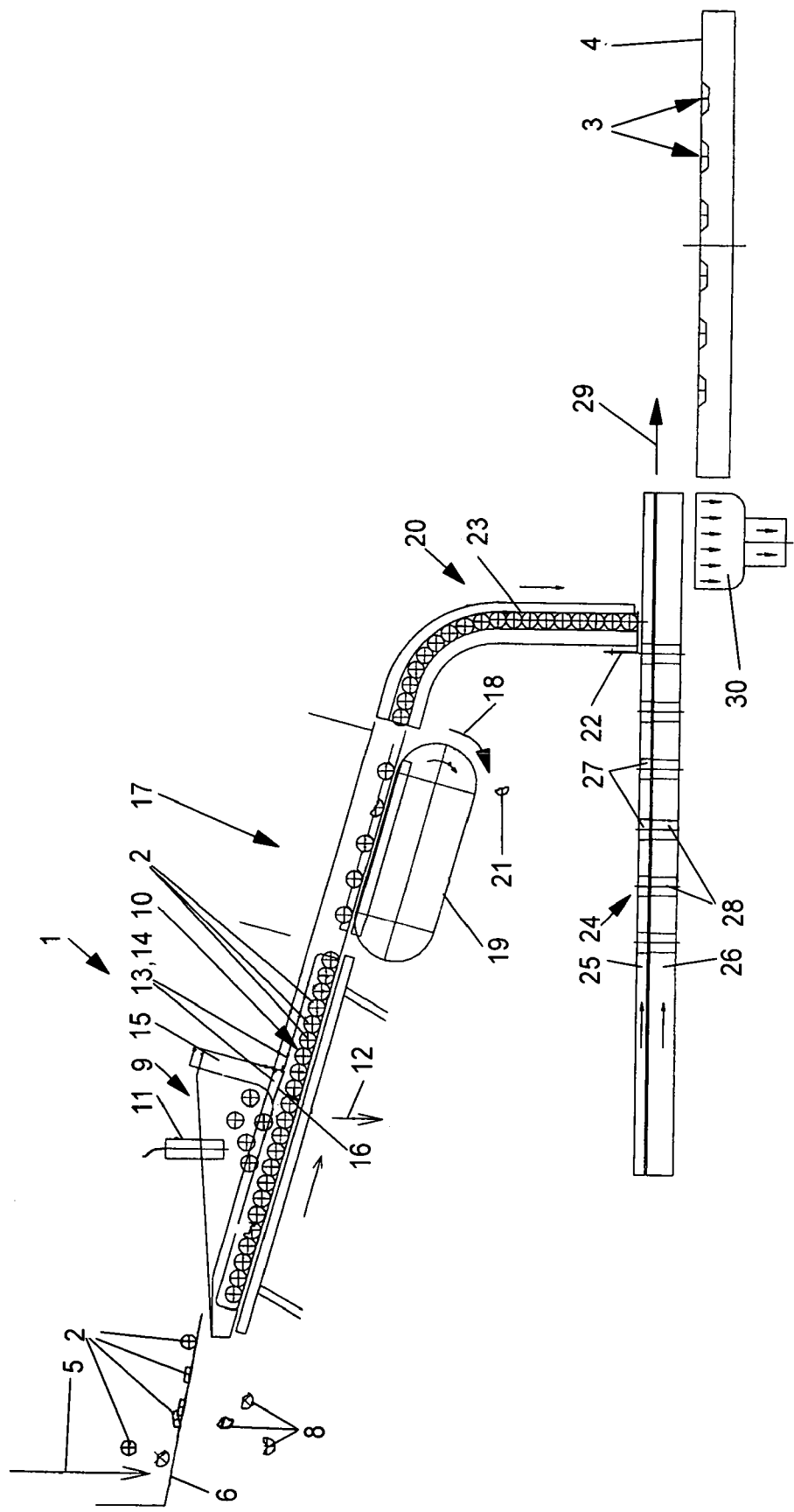
FIG. 1 is a schematic side view of a first exemplary embodiment of the novel apparatus.

Referring now in greater detail to the drawings, FIG. 1 schematically illustrates an exemplary embodiment of the novel apparatus 1. With the apparatus 1, fragile tablets 2 are placed into pockets 3 of a thermoformed bottom foil 4. The tablets 2 are delivered by a tablet press or from a reservoir (not illustrated), and they move according to arrow 5 to reach a declined slide 6 in an unsorted way. The slide 6 may also be designed as an oscillating conveyor and the like, and it may be designed to deliver tablets 2 in a time-wise controlled way. A part of the bottom portion of the slide 6 or the entire slide 6 may be designed as a perforated plate including openings 7 (see FIG. 4). The diameter of the openings 7 is smaller than the diameter of the tablets 2 such that only pieces 8 of tablets 2 fall through the openings 7 the size of which is smaller than the diameter of an entire tablet 2. It is to be understood that not only pieces 8, but also dust of the material of the tablets 2 may pass through the openings 7.

An erecting station 9 is located downstream of the exit of the slide 6, the erecting station 9 serving to bring the tablets 2 in an upright position. In other words, the erecting station 9 serves to rotate (or pivot) the tablets 2 being delivered on the slide 6 in a flat position to reach a rotated position in which the axis of the disc-like body of the tablet 2 is arranged to be entirely or at least partly horizontal. For reasons of simplicity, it is now assumed that the tablets 2 are moved to reach a complete upright position such that they are supported on the edge of the tablet 2 and such that they are located one after the other to form tablet lines 10 in which tablets 2 are located along a line such that they contact one another, as this is illustrated in FIG. 1. In this way, a plurality of adjacent and separately guided tablet lines 10 are realized no matter how many tablets 2 are arranged in the lines 10. One or more sensors 11 are located in the region of the erecting station 9, the at least one sensor 11 determining the filling level of the erecting station 10. The signals produced by the at least one sensor 11 serve to change the production velocity of the tablet press. With such a control, it is desired to always supply a sufficient amount of tablets 2 in the erecting station 9. It is to be understood that not all tablets 2 contained in the erecting station 9 are necessarily undamaged. Instead, there are also damaged tablets among the tablets 2 which could not be discharged through the opening 7 arranged in the slide 6. It is already to be seen in FIG. 1 that the tablets 2 located in the upright position substantially move on by rolling which results in very little stress causing the danger of breakage of the fragile tablets 2. The erecting station 9 is designed to be permeable in a downward direction such that small pieces and dust of tablets 2 can be discharged according to the direction of arrow 12. It is also possible to arrange a suction apparatus below the erecting station 9. The erecting station 9 includes lamellas 13, 14 forming gaps and passages there between. The design will be explained in greater detail herein below. The lamellas 13 and 14 substantially extend in a downwardly declined direction and along the length of the erecting station 9. The lamellas 13 and 14 include protrusions 15 protruding in a perpendicular direction and in an upward direction. The intermediate spaces between the protrusions 15 are designed to be closed in the protruding region such that a weir serving to collect the tablets 2 in the conveying path is formed. Passages 16 are located at the transition point of the protrusions 15 to the lamellas 13 and 14. The passages 16 are designed to be slightly higher than the diameter of a tablet 2 and slightly wider than the thickness of the tablets 2. In this way, only one tablet 2 may pass through this location at which the passage 16 is connected to a gap. A passage 16 is connected to each row of tablets 2 such that there is a plurality of passages 16. Downstream of the passages 16, the tablets 2 are arranged to form the tablet lines 10.

A control station 17 is located downstream of the erecting station 9 as seen in the direction of movement of the tablets 2. The control station 17 includes an endless belt 19 which is driven in the direction of arrow 18. For example, the belt 19 is designed as a cam belt providing reception locations for the tablets 2 in which the tablets 2 are supported in a spaced apart manner, meaning in an individual way without contacting one another. The design and functionality of the control station 17 will be explained in greater detail herein below.

A storage and delivery station 20 is connected to the control station 17. The station 20 includes a plurality of adjacent bent channels leading in a downward direction. The tablets 2 are stored in these channels as tablet lines 10 in an adjacent way. It is also possible to arrange the channels to slightly branch off from one another. While the tablets 2 are individualized in the region of the control station 17 to be able to check them with respect to damages and to sort out damaged tablets 21, for example, only undamaged tablets 2 are stored in the storing and delivery station 20 as lines of tablets 10. The storing and delivery station 20 includes a translating element 22 which is designed and arranged to be moved to alternately reach two different positions. In the first position, the element 22 closes the storing and delivery station 20 such that no tablets 2 are delivered. In the second position, the element 22 opens the storing and delivery station 20 such that tablets 2 are delivered in a controlled way. The storage and delivery station 20 includes a plurality of spaced apart adjacent paths 23 in which the respective tablet lines 10 are formed and moved in a downward direction, respectively.

A transfer unit 24 cooperates with the end of the storing and delivery station 20. The transfer unit 24 serves to receive the tablets 2 in their upright position corresponding to the arrangement of the pockets in the bottom foil 4 and to transfer the tablets 2 into a position above the pockets 3 and to rotate the tablets 2 back into their flat position from the upright position directly before delivery. The tablets 2 need to be located in their flat position to be received in the pockets 3. For this purpose, the transfer unit 24 includes two plates 25 and 26, the plates 25 and 26 being arranged to be substantially horizontal and such that the plate 25 is supported on top of the plate 26. The plates 25 and 26 are designed and arranged to be commonly moved according to the direction of arrow 29 to be moved above the bottom foil 4 according to the arrangement of the pockets 3. The upper plate 25 includes openings or impressions 27. The impressions 27 have a rectangular cross-section corresponding to the diameter and the thickness of the tablets 2. The impressions 27 extend in a vertical direction through the upper plate 25. Channels 28 are located in the lower plate 26, the channels being designed to be inclined or curved. The plates 25 and 26 are not only designed and arranged to be commonly moved according to arrow 29, but also with respect to one another to reach at least two positions. In the first position, the impressions 27 of the upper plate 25 are covered by the lower plate 26. In the second position, the channels 28 are connected to the impressions 27. This design will be explained in greater detail herein below. The transfer station 24 and the two plates 25 and 26 are associated with a unit 30 for sucking off dust and small pieces of tablets from the impressions 27 and the channels 28 being connected thereto.

Figure 2:
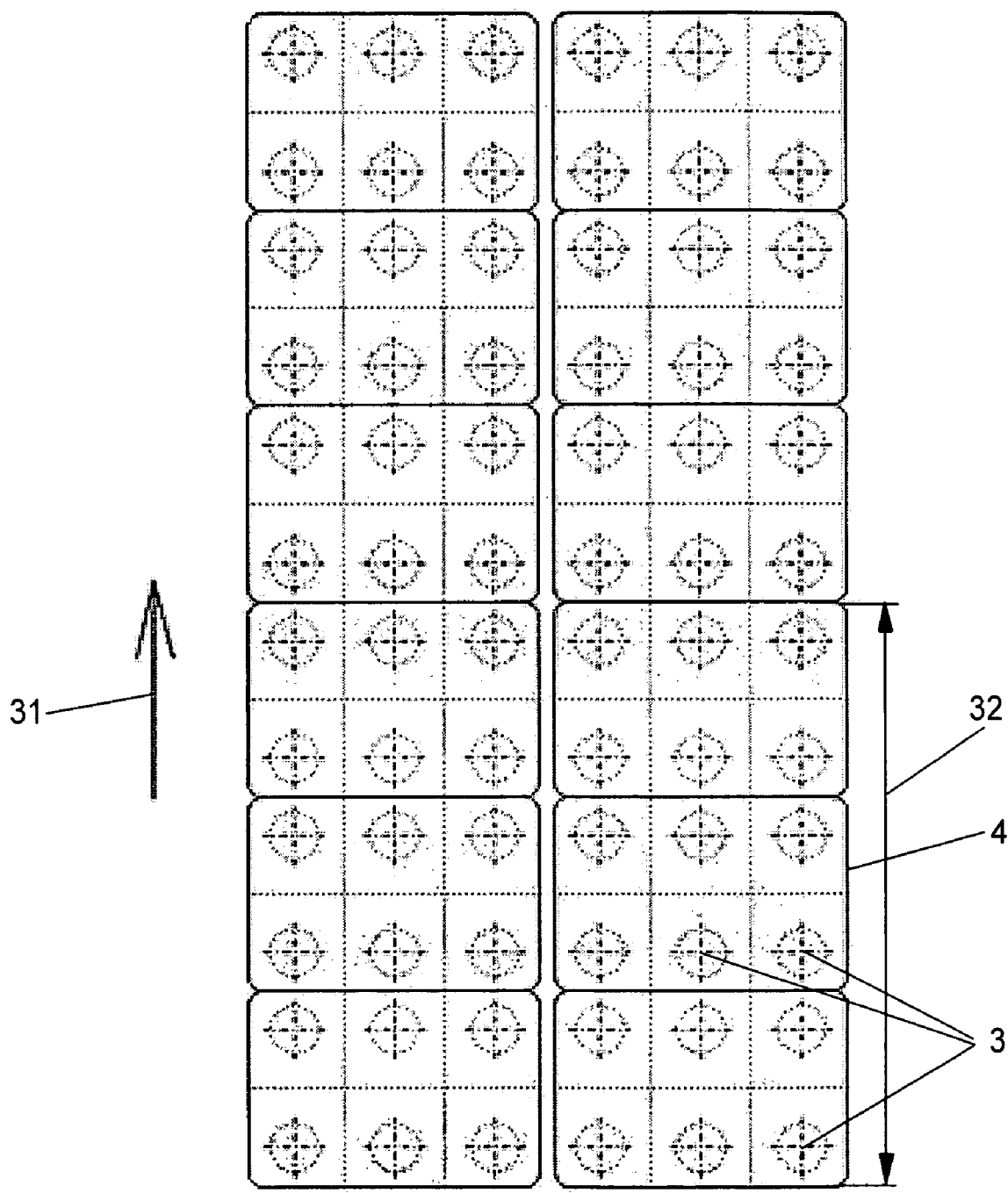
FIG. 2 is a top view of a thermoformed bottom sheet.

It is to be seen from FIGS. 1 and 2 that the bottom foil 4 being moved forward according to arrow 31 in a clocked manner includes the pockets 3 according to an arrangement in the form of a grid. In the illustrated exemplary embodiment, six pockets 3 are arranged in series along the working width such that the upper plate 25 of the transfer unit 24 also includes six impressions 27 being located at the corresponding distance. In the illustrated exemplary embodiment, during each clocked forward movement about the distance 32, 36 pockets 3 to be filled with tablets 2 are provided. Correspondingly, the upper plate 25 also includes 36 impressions 27 being arranged in a way to correspond to the grid. It is to be understood that the storing and delivery station 20 also includes six paths 23 being located one next to the other. Furthermore, it is to be understood that it is also possible to use any different grid arrangement. To process different grid arrangements in the same apparatus 1, the elements and stations are designed as form elements which can be replaced.

Figure 3:
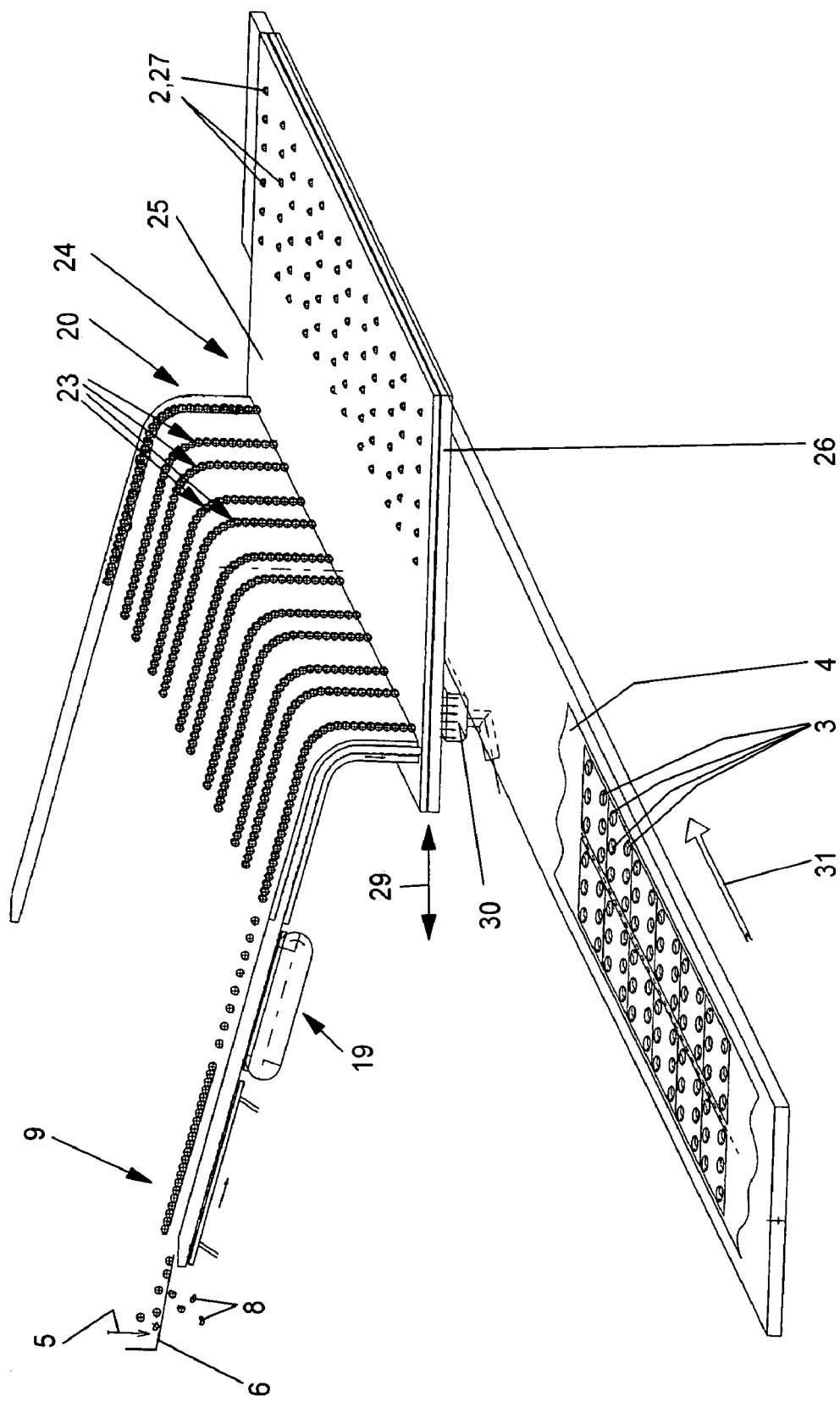
FIG. 3 is a schematic perspective view of the novel apparatus.

FIG. 3 further illustrates the relative arrangement of the paths 23 of the storing and delivery station 20 for an exemplary embodiment in which the distance 32 does not cover six rows, but instead twelve rows. Accordingly, the upper plate 25 includes 72 impressions 27 to be filled with tablets 2. It is to be understood that the erecting station 9 and the control station 17 are also arranged twelve times to be capable of processing the tablets 2. However, for reasons of clarity of the drawings, only one station 9 and one station 17 are illustrated. Furthermore, FIG. 3 makes it clear that the apparatus 1 may be designed, arranged and adapted, respectively, to process each desired grid arrangement.

Figure 4:
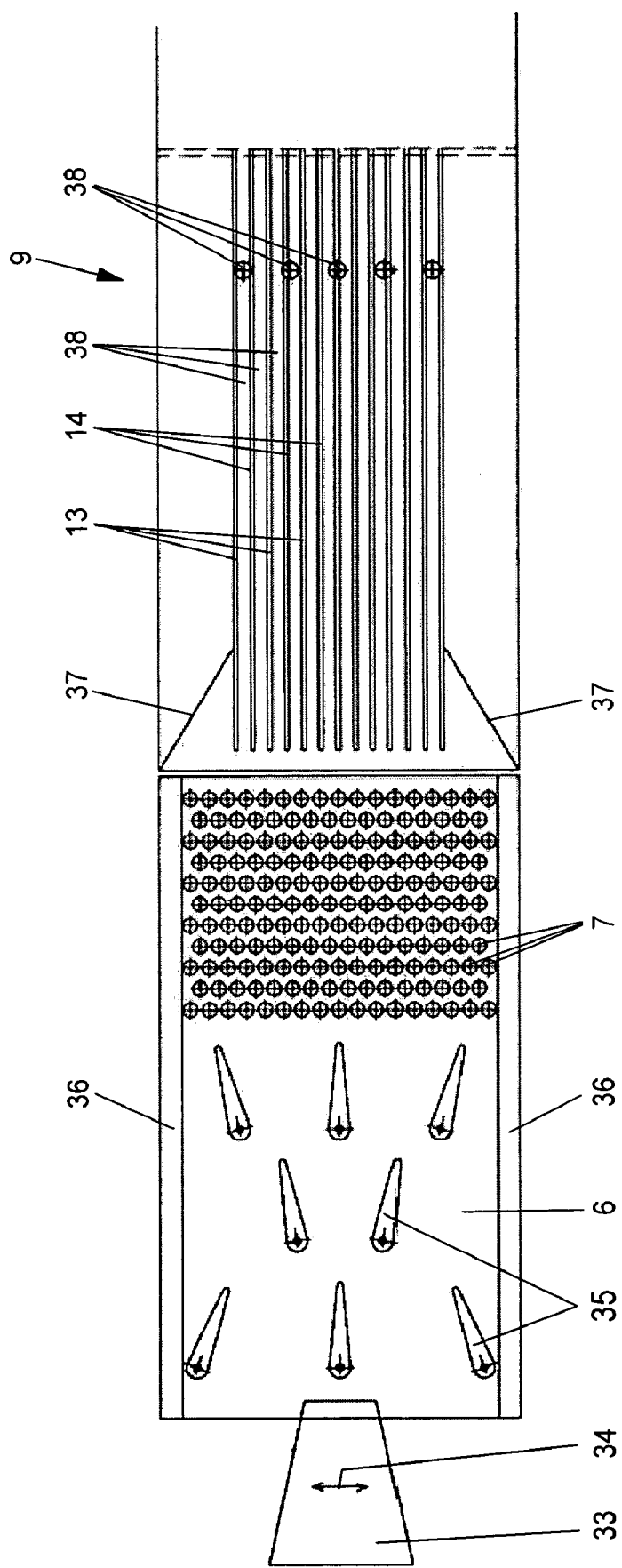
FIG. 4 is a top view of the beginning portion of the novel apparatus.

FIG. 4 illustrates a top view of the elements located between the tablet press and the erecting station 9. The tablet press (not illustrated) may include an exit 33 which is driven to move back and forth to distribute the tablets 2 to be delivered according to double arrow 34 in a direction transverse to the working direction. Wings 35 or different guiding elements may be arranged in the first portion downstream of the slide 6. These wings 35 or different guiding elements are designed and arranged such that the tablets 2 (not illustrated) are more or less uniformly distributed over the working width of the slide 6 being limited by the side walls 36. The following openings 7 allow for dust and broken pieces of tablets 2 to fall down such that substantially only undamaged tablets 2 and such tablets 2 only having comparatively small damages enter the erecting station 9. The flow of tablets 2 is concentrated by the guiding plates 37, and it is distributed in a way to reach the region of the lamellas 13 and 14. The tablets 2 (not illustrated) are still located in their flat unsorted position. It is also possible that some tablets 2 are slightly inclined with respect to one another or that they are placed on one another. Gaps 38 are formed between adjacent lamellas 13 and 14. In the exemplary embodiment illustrated in FIG. 3, there are twelve gaps 38. It is possible to arrange sensors 11 to control the wings 35 and to make sure that there is a sufficient number of tablets 2 at all places over the working width of the lamellas 13, 14.

Figure 5:
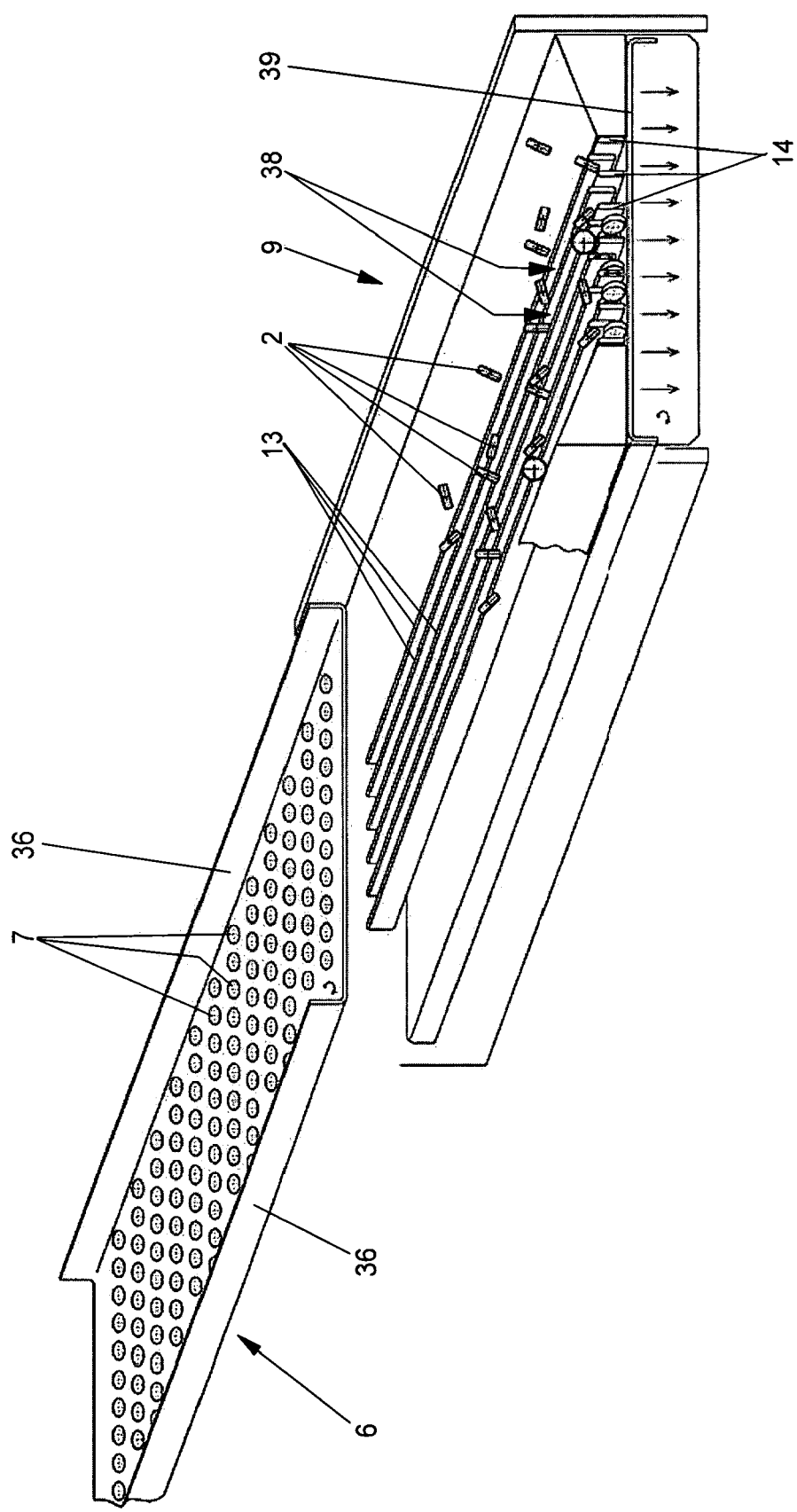
FIG. 5 is a schematic three-dimensional view of the erecting station.

FIG. 5 further illustrates this portion already illustrated in FIG. 4, but now with a different number of lamellas 13 and 14 for reasons of clarity of the drawings. Some tablets 2 are illustrated in the region of the erecting station 9. It is to be understood that the number of tablets 2 usually is greater and that they are located closer to one another. It is schematically illustrated that the lamellas 14 are located in their lower position, while the lamellas 13 are just located in their raised position. Consequently, the tablets 2 can slide into the gaps 38 formed between the lamellas 13 and 14 in a lateral direction in a way to be moved from the flat position into the upright position being rotated by 90° with respect to the flat position. Some of the upright tablets 2 are illustrated. A continuous bottom 39 is located below the gaps 38. The tablets 2 with their edges are supported on the bottom 39 in an upright position, the tablets 2 moving in a forward direction by rolling within the gaps 38. It is easily imaginable that gate-like passages 16 are formed at the end or in the middle portion, meaning in the region of the protrusions 15, as indicated in FIG. 1. Only one tablet 2 can pass through the respective passage 16 at a time by rolling within a path and a gap 38, respectively. In this way, the tablets 2 form lines of tablets 10 during and after passage.

Figure 6:
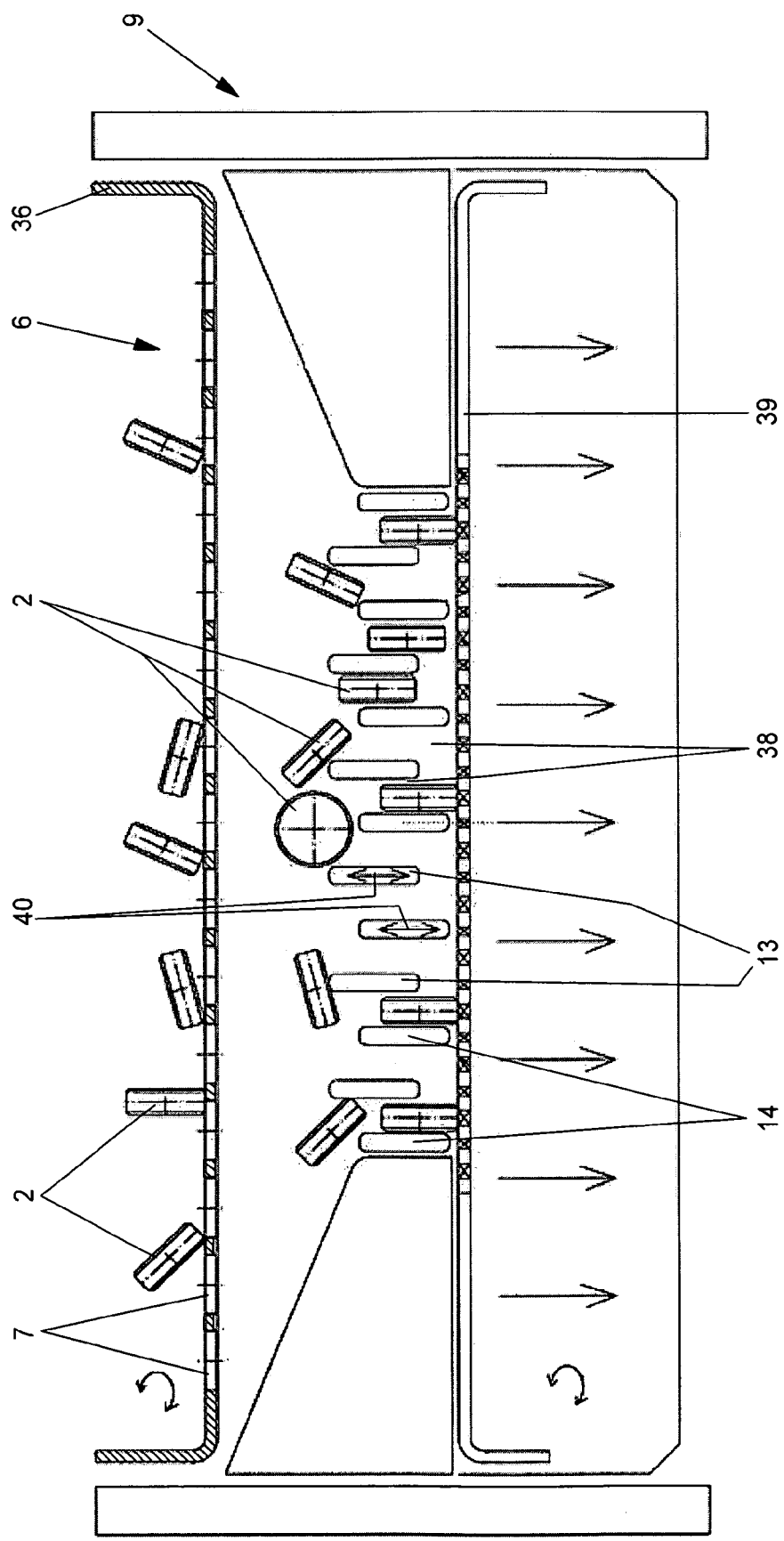
FIG. 6 is a vertical sectional view through the erecting station.

FIG. 6 further illustrates the erecting process of the tablets 2 in the erecting station 9. Furthermore, the slide 6 with its openings 7 is illustrated in the upper portion. The slide 6 serves to supply the tablets 2 in an unsorted relative position. In this position, the tablets 2 enter the erecting station 9 including the lamellas 13 and 14 which can be moved in a horizontal direction according to arrows 40. It is to be understood that the lamellas 13 and 14 may be supported and arranged to be movable with respect to one another in a vertical direction. It is desired to attain supporting locations for inclined planes at which the tablets 2 can slide down into the gaps 38 resulting in the tablets 2 being brought into their upright position. As illustrated in FIG. 6, the tablets 2 are then supported on their edge or rim, and they move on in a forward direction by rolling. It is to be understood that all gaps 38 are filled with upright tablets 2 in this way. The bottom 39 may be designed as a perforated bottom. The "standing" tablets 2 are supported on the bottom 39. Dust and smaller pieces of tablets can fall down through the bottom 39 and/or they can be sucked off. The lamellas 13 may be arranged on a common lamella axis to be pivotable and to be moved by a crank mechanism or a cam mechanism with a vertical component of movement to realize the erecting movement of the tablets 2.

FIG. 7 further illustrates the design and functionality of the control station 17. As it is already to be seen in FIG. 1, the tablets 2 of the line of tablets 10 are individualized at the transition between the erecting station 9 and the control station 17. Individualization of the tablets 2 means that the tablets 2 are moved to be located at a distance with respect to one another. It makes sense to design and arrange the endless rotating belt 19 in an inclined way to make it possible that the tablets 2 are not only received with their edge, but also with one of their faces. The axis of the tablet 2 is no longer arranged to be horizontal, but instead to be inclined. This relative position allows for optical systems including a majority of cameras 41 to be located in an adjacent manner with small space requirements as it corresponds to the lines of tablets 10 being located one next to the other. A tablet 21 which is damaged in the region of its edge is determined by the camera 41 and singled out, while undamaged tablets 2 are transmitted to the storing and delivery station 20. Removal of a damaged tablet 21 may be realized by an air flow coming from a nozzle 42 and through a schematically illustrated opening being located in the belt 19. Alternatively or additionally, a sucking off apparatus may be operated according to arrows 43. It is to be understood that the removal of a damaged tablet 21 is controlled in response to the signals of the respective camera 41. The tablets 2 and 21, respectively, are supported on the belt 19 at an inclined orientation to allow for a scale-like covered arrangement by the majority of cameras 41 within a small space. It is possible that the tablets 2 reach their fully upright position after a rotation when entering the storing and delivery station 20.

Figures 8, 9:
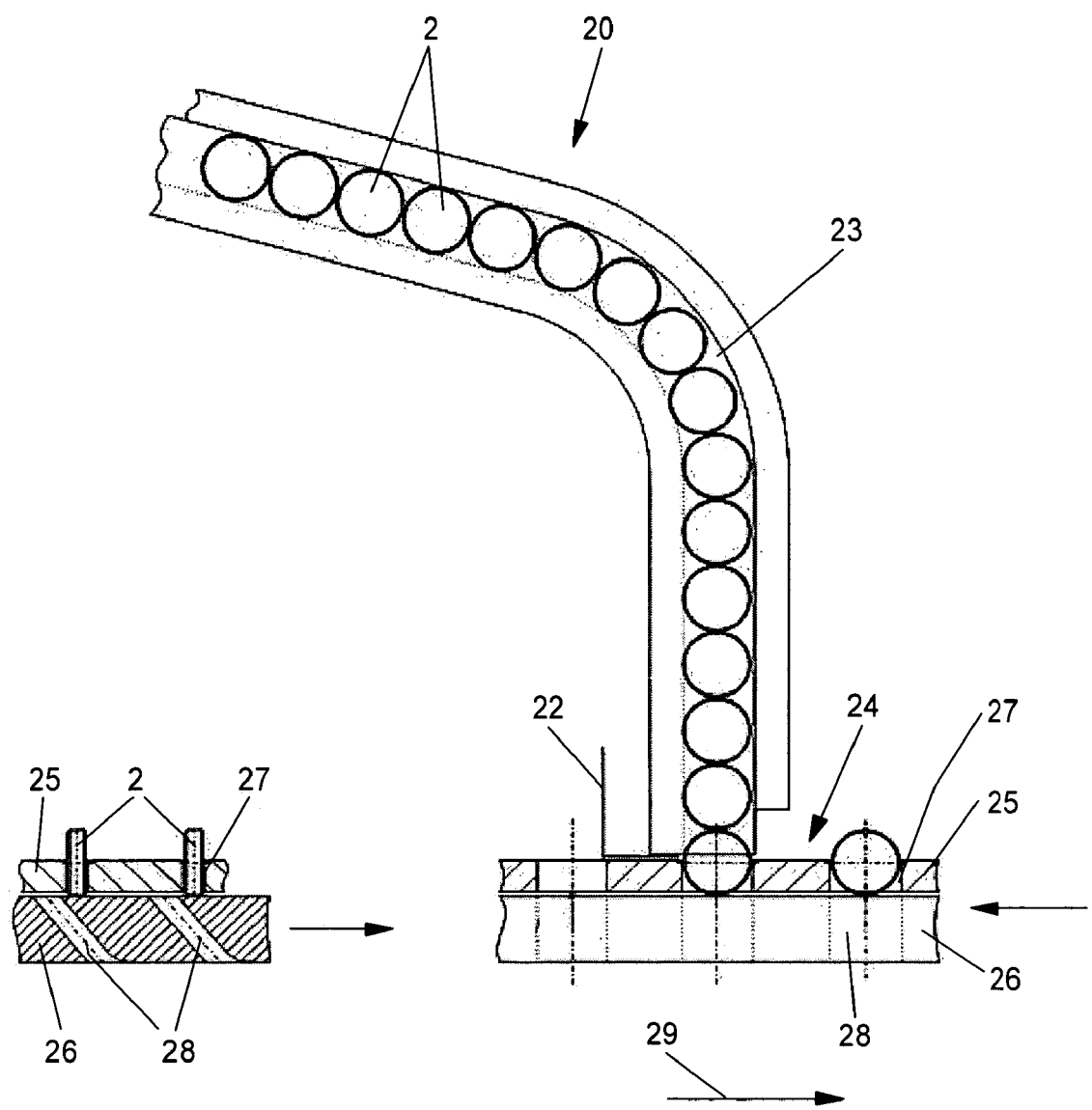
FIG. 8 is a schematic side view of a storing and delivering station and of a part of the transfer station.
FIG. 9 is a vertical sectional view of the transfer station in a viewing direction rotated by 90°.

FIG. 8 further illustrates the storing and delivery station 20. In this case, only one path 23 including the stored tablets 2 is illustrated. The walls of the path 23 end at different heights with respect to the transfer unit 24. There is a free space beginning at the bottom of the impression 27 and extending to one of the side walls. The free space is slightly greater than the diameter of a tablet 2. The translating and pushing element 22 is located in its opened position. The impressions 27 are closed towards the bottom side by the lower plate 26. The transfer unit 24 is moved below the storing and delivery station 20 according to arrow 29. One tablet 2 enters an impression 27 at each lower end of the storing and delivery station 20. The tablets 2 are stored in the impressions 27. It is to be understood that this occurs simultaneously in a plurality of paths 23 of the storing and delivery station 20 such that all impressions 27 of the transfer unit 24 are filled and such that the number of tablets 2 corresponds to the predetermined grid of pockets to be filled at a time.

FIG. 9 is a sectional view illustrating a cross-section as seen from a viewing direction rotated by 90°. One can see the tablets 2 as they "stand" in the impressions 27. It is also to be seen that the impressions 27 are closed towards the bottom side due to the relative position of the plates 25 and 26 such that the channels 28 are not connected to the impressions 27. In this position, the plates 25 and 26 of the transfer unit 24 are commonly moved above the bottom foil 4 according to arrow 29, the exits of the channels 28 getting into a certain relationship to the pockets 3. Due to a relative movement of the plate 25 and 26 with respect to one another, the impressions 27 get connected to the channels 28 such that the tablets 2 are placed in the pockets 3 simultaneously and in a way corresponding to the grid. The tablets 2 are rotated back from the upright position into the flat position.

Figure 10:
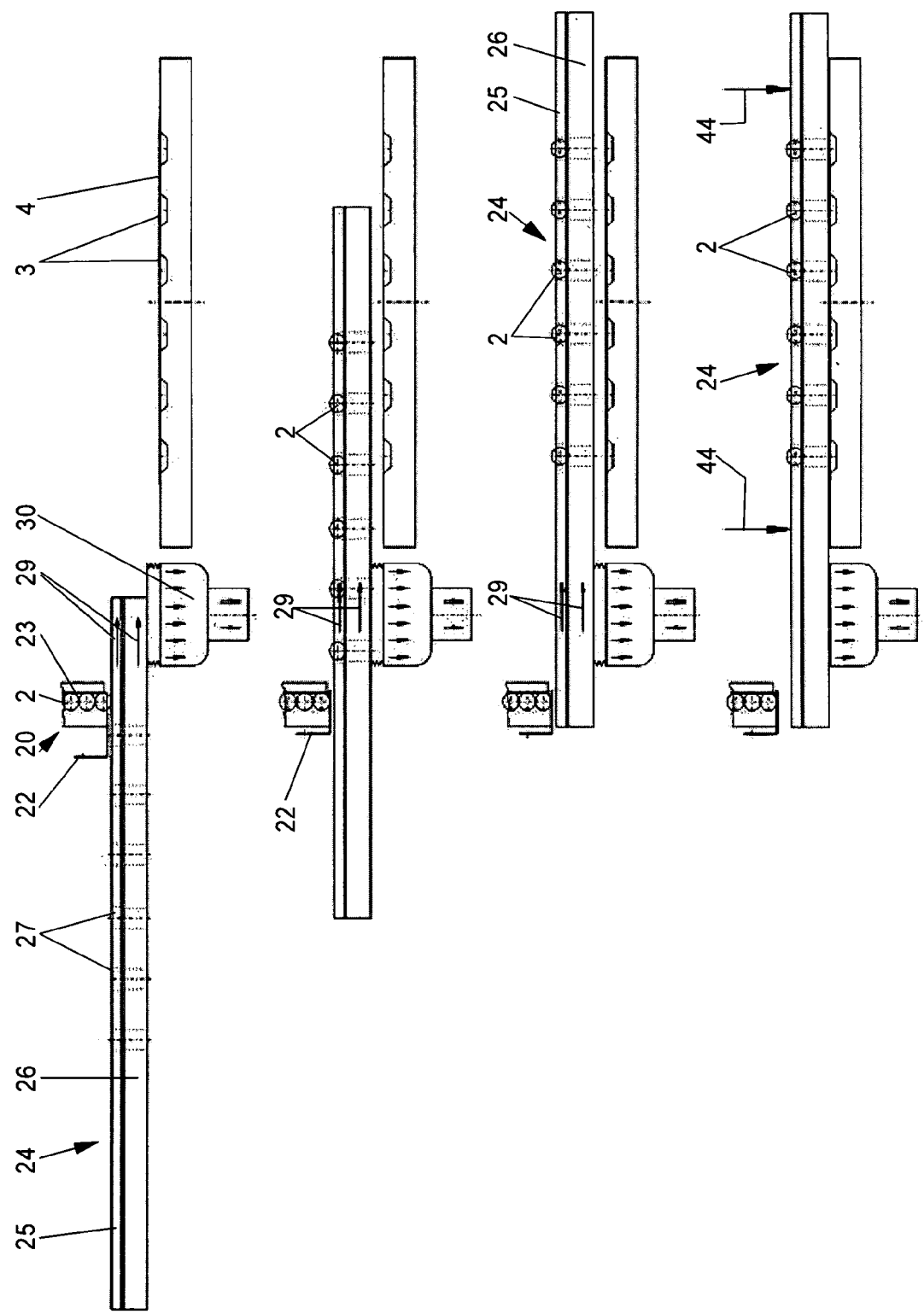
FIG. 10 is a view illustrating the first four method steps of the transfer unit.
Figure 11:
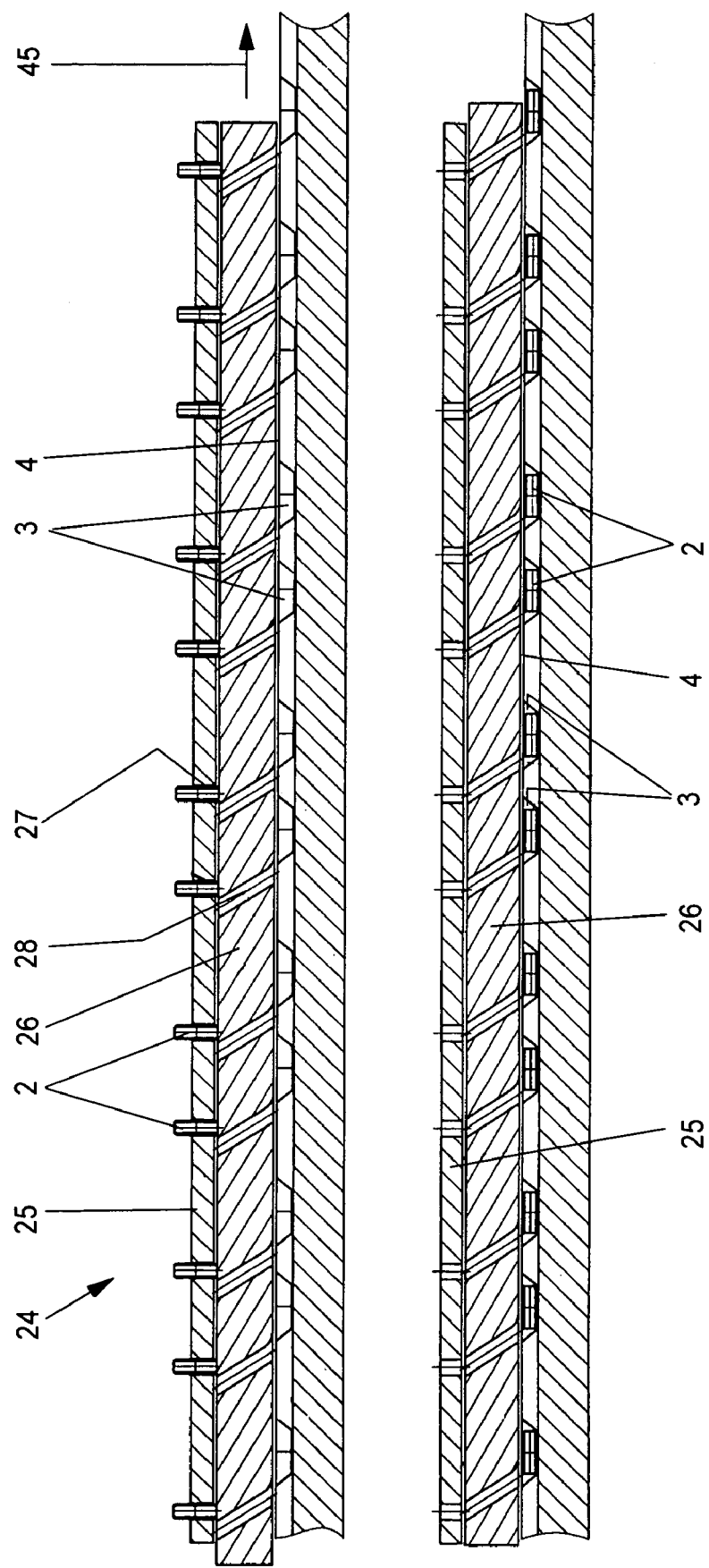
FIG. 11 is a view illustrating the relative movement of the plates of the transfer unit.

The operation of the transfer unit 24 will be explained with respect to FIGS. 10 to 12 in separate steps. In the starting position as illustrated in FIG. 10, the transfer unit 24 is located below the storing and delivery station 20. The translating elements 22 are opened. The two plates 25 and 26 are located at such a relative position with respect to one another that the impressions 27 are closed at the bottom side. From this position, the transfer unit 24 passes below the exits of the storing and delivery station 20. During this movement, the tablets 2 are separately placed into one of the impressions 27 one after the other until the array of impressions 27 has been completely filled with upright tablets, as this is illustrated in the second illustration of FIG. 10. The translating elements 22 are moved into the closed position such that the tablets are prevented from further exiting.

In the third step, the transfer unit 24 reaches its exact position above the pockets 3 formed in the bottom foil 4. In the fourth step, the transfer unit 24 is moved in a downward direction according to arrows 44 to reduce the height of fall. FIG. 11 further illustrates the relative position of the elements in this step once again in a cross-section in a direction of view being rotated by 90°. In the upper illustration of FIG. 11, the impressions 27 are still closed at the bottom side such that the tablets 2 are located in the rotated upright position. In the following, for example, the lower plate 26 is moved in the direction of arrow 45 such that the channels 28 get into alignment with the impressions 27. As soon as this has been realized, the tablets 2 slide down in a gentle way and at a small height of fall to reach the pockets 3 of the bottom foil 4.

Figure 12:
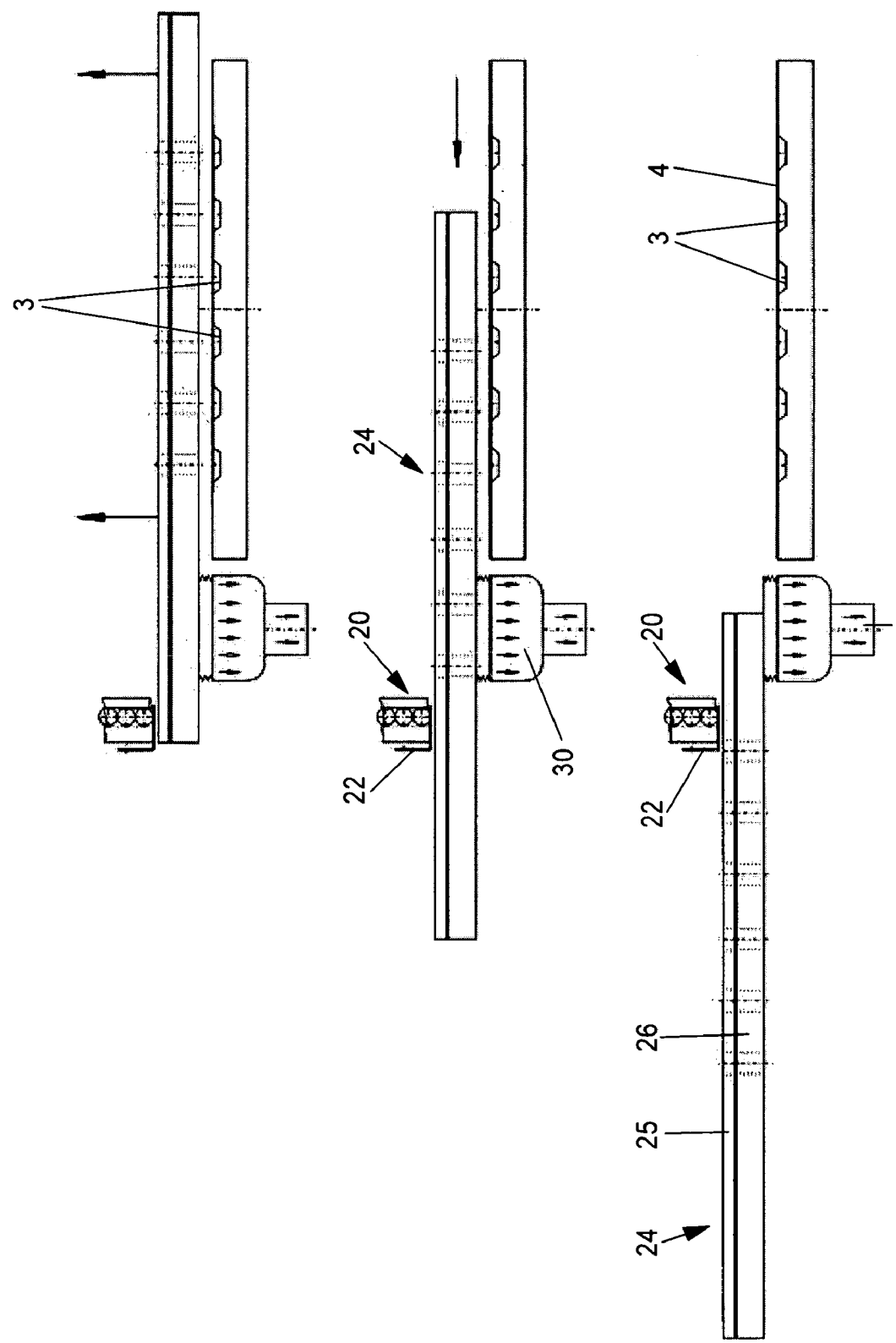
FIG. 12 is a view illustrating further method steps of the transfer unit.

After having placed the tablets 2 into the pockets 3 of the bottom foil 4 (while the tablets 2 are simultaneously rotated back to reach the flat position), the transfer unit 24 is lifted according to the additional step illustrated in the upper portion of FIG. 12. The lowering movement according to arrows 44 and the lifting movement in the opposite direction may be chosen to be adjustable. At the same time or at a slightly different point in time, the bottom foil 4 is further moved on by one cycle such that the array of empty pockets 3 is moved forward. During the backward movement of the transfer unit 24 against the direction of arrow 29, the unit 30 becomes active to suck off dust from the impressions 27 and the channels 28 connected thereto and to thus clean the transfer unit 24. Alternatively, it is possible to operate the unit 30 without interruption, the unit 30 being connected to negative pressure. As soon as the transfer unit 24 has reached its starting position, the plates 25 and 26 are once again moved with respect to one another such that the impressions 27 are closed towards the bottom side. Then, the next cycle follows.

Figure 13:
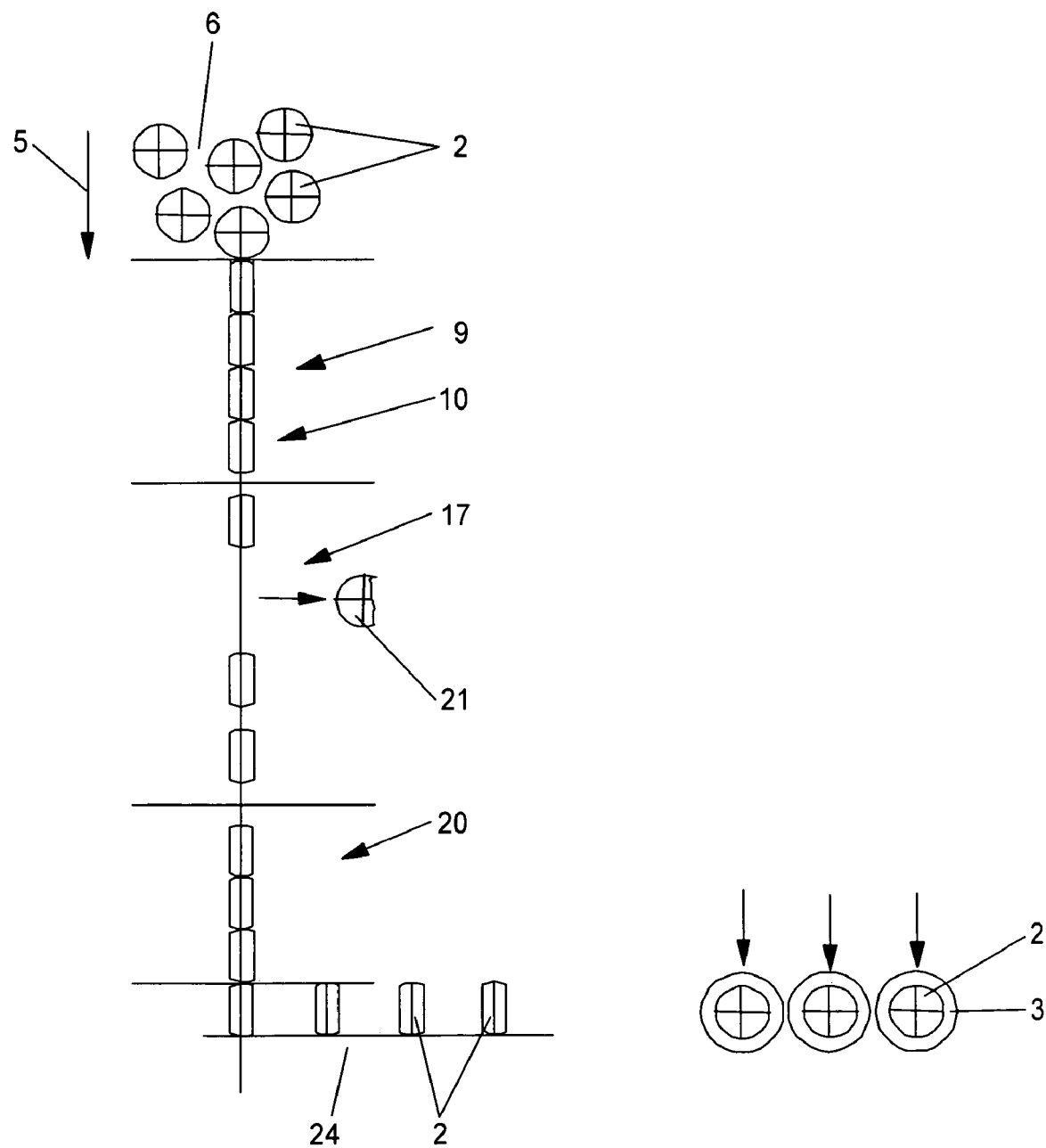
FIG. 13 is a view schematically illustrating the step of erecting the tablets and of rotating them back into the flat position.

FIG. 13 once again further illustrates the steps following one another with which the tablets 2 are treated and finally placed into the pockets 3. At first, the tablets 2 are located in the region of the slide 6 in an unsorted manner and in their flat position. They have reached this position after exiting from the tablet press in the direction of arrow 5. In the region of the following erecting station 9, the tablets 2 are moved to reach their upright position and to form tablet lines 10. In the following control station 17, the tablets 2 are individualized, and they are separately controlled, the tablets 2 either passing through the control station 17 in their upright position or in an inclined position. Damaged tablets 21 are being removed. In the following storing and delivery station 20, the checked undamaged tablets 2 are once again stored while they are still located in their upright position. This also applies to the following transfer unit 24. The tablets 2 are located in the impressions 27 of the transfer unit 24 as it corresponds to the arrangement of the bottom foil 4. Finally, the tablets 2 are placed into the pockets 3 of the bottom foil 4, the tablets 2 then being rotated back into their flat position.

Figure 14:
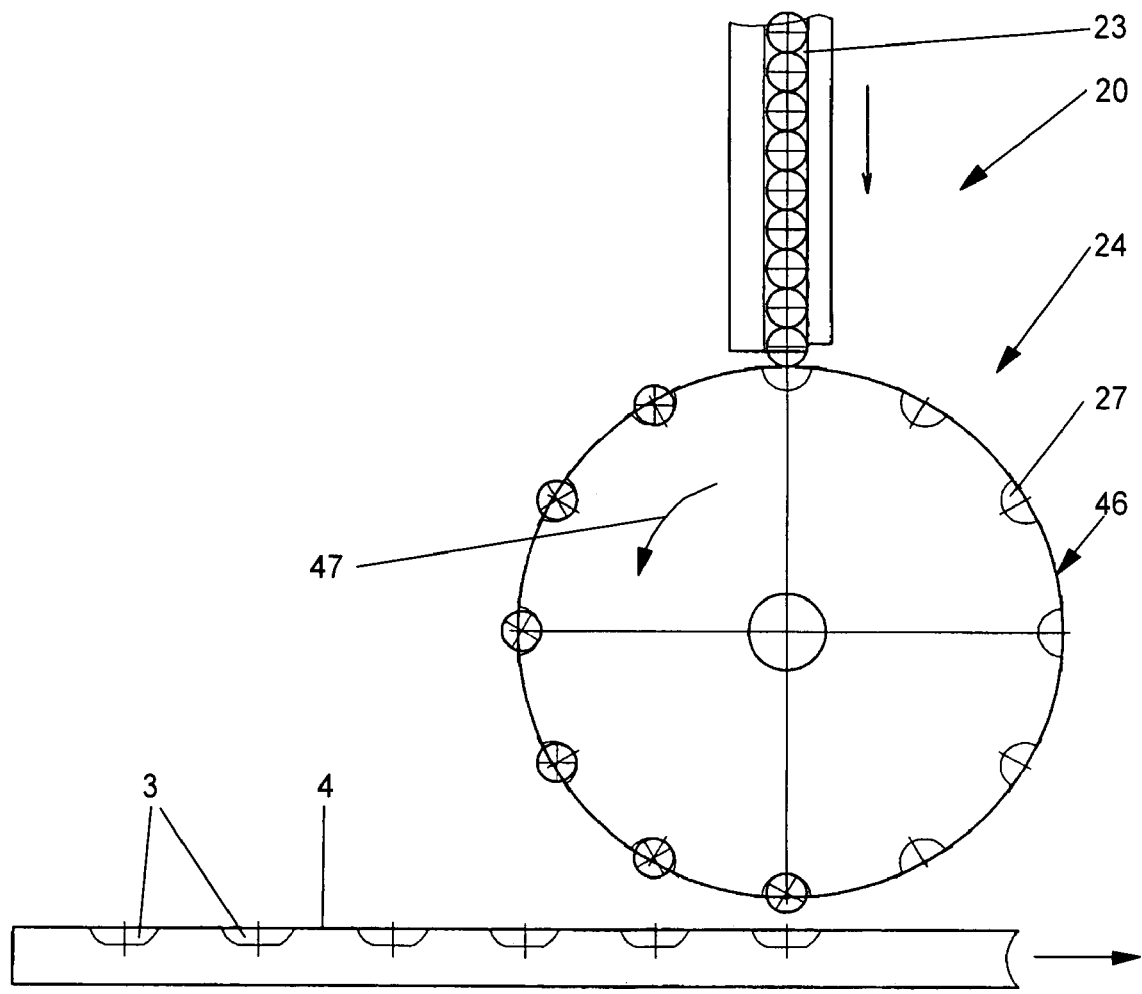
FIG. 14 is a view of another exemplary embodiment of the novel transfer unit.

FIG. 14 further illustrates another exemplary embodiment of the novel transfer unit 24. The transfer unit 24 is designed as a dosing roller 46 including the impressions 27 at its circumference. The impressions 27 are connected to a vacuum source such that they are carried with the dosing roller 46 about half the circumference of the dosing roller 46 during continuous rotation of the dosing roller 46 according to arrow 47. Then, they are exactly positioned in the pockets 3 of the bottom foil 4. The placement can be realized directly or by a channel (not illustrated) serving to realize the rotation back into the flat position. It is to be understood that the tablets 2 are always placed in series. The drive of the dosing roller 46 and the drive pulling the bottom foil 4 are not continuously operated in this exemplary embodiment.

Many variations and modifications may be made to the preferred embodiments of the invention without departing substantially from the spirit and principles of the invention. All such modifications and variations are intended to be included herein within the scope of the present invention, as defined by the following claims.

We claim:

1. A method of placing tablets into pockets of thermoformed bottom foil, the tablets having two faces and a rim portion, said method comprising the steps of:
   accumulating the tablets as they are located in their flat position in which the tablets are supported on one of the faces;
   rotating the tablets such that they reach an approximately upright position in which the tablets are at least partly supported on the rim portion;
   forming a plurality of lines of approximately upright tablets;
   rotating the approximately upright tablets back into their flat position; and
   placing the tablets into the pockets of the bottom foil as the tablets are located in their flat position.

2. The method of claim 1, further comprising the step of removing pieces and dust of damaged tablets.

3. The method of claim 1, wherein the tablets are rotated by approximately 90° in the first rotating step.

4. The method of claim 2, wherein the tablets are rotated by approximately 90° in the first rotating step.

5. The method of claim 1, further comprising the steps of: individualizing the approximately upright tablets as they are located in the lines of tablets;
   checking the individualized tablets with respect to damages; and
   removing damaged tablets.

6. The method of claim 2, further comprising the steps of:
   individualizing the approximately upright tablets as they are located in the lines of tablets;
   checking the individualized tablets with respect to damages; and
   removing damaged tablets.

7. The method of claim 3, further comprising the steps of:
   individualizing the approximately upright tablets as they are located in the lines of tablets;
   checking the individualized tablets with respect to damages; and
   removing damaged tablets.

8. The method of claim 5, further comprising the steps of:
   accumulating the undamaged and approximately upright tablets; and
   introducing the undamaged and approximately upright tablets into a plurality of impressions being located in a transfer unit, the second rotating step taking place during passage of the tablets through the transfer unit.

9. The method of claim 6, further comprising the steps of:
   accumulating the undamaged and approximately upright tablets; and
   introducing the undamaged and approximately upright tablets into a plurality of impressions being located in a transfer unit, the second rotating step taking place during passage of the tablets through the transfer unit.

10. The method of claim 7, further comprising the steps of:
    accumulating the undamaged and approximately upright tablets; and
    introducing the undamaged and approximately upright tablets into a plurality of impressions being located in a transfer unit, the second rotating step taking place during passage of the tablets through the transfer unit.

11. An apparatus for placing tablets into pockets of a thermoformed bottom foil, the tablets having two faces and a rim portion, said apparatus comprising:
    an erecting station, said erecting station being designed and arranged to rotate the tablets from a flat position in which the tablets are supported on one of the faces into an approximately upright position in which the tablets are at least partly supported on the rim portion; and
    a transfer unit, said transfer unit including a plurality of channels, said channels being designed and arranged to rotate the tablets from the approximately upright position back into the flat position, said transfer unit being designed and arranged to place the tablets into the pockets of the bottom foil as the tablets are located in their flat position.

12. The apparatus of claim 11, further comprising a unit for removing pieces and dust of damaged tablets.

13. The apparatus of claim 12, further comprising:
    a unit for accumulating the tablets as they are located in their flat position;
    a unit for forming a plurality of lines of approximately upright tablets.

14. The apparatus of claim 11, wherein said channels are designed to be inclined.

15. The apparatus of claim 11, wherein said channels are designed to be arcuate shaped.

16. The apparatus of claim 11, wherein
    the tablets have a thickness and a diameter, said erecting station includes a plurality of lamellas, said lamellas substantially extending in a vertical direction and being designed and arranged to be movable in a vertical direction, said lamellas being designed and arranged to form gaps between two adjacent lamellas, said gaps having a size corresponding to the thickness of the tablets, said gaps being designed to be closed at a bottom side, and said erecting station includes a plurality of protrusions having dimensions corresponding to the thickness and the diameter of the tablets.

17. The apparatus of claim 11, wherein said transfer unit includes a top plate and a bottom plate,
    said top plate being placed on said bottom plate,
    said top plate and said bottom plate substantially extending in a horizontal direction,
    said top plate and said bottom plate being designed and arranged to be commonly movable and to be movable with respect to one another,
    said bottom plate including a plurality of impressions, said impressions being designed and arranged to receive tablets in a way corresponding to the arrangement of the pockets in the bottom foil, and
    said bottom plate including said channels.

18. The apparatus of claim 17, wherein said transfer unit includes a top plate and a bottom plate,
    said top plate being placed on said bottom plate,
    said top plate and said bottom plate substantially extending in a horizontal direction,
    said top plate and said bottom plate being designed and arranged to be commonly movable and to be movable with respect to one another,
    said bottom plate including a plurality of impressions, said impressions being designed and arranged to receive tablets in a way corresponding to the arrangement of the pockets in the bottom foil, and
    said bottom plate including said channels.

19. The apparatus of claim 17, further comprising a storing and delivery station,
    said storing and delivering station being arranged between said erecting station and said transfer unit,
    said storing and delivery station being designed and arranged to accumulate the lines of tablets and to deliver the tablets into said impressions of said transfer unit corresponding to the arrangement of the pockets in the bottom foil.

20. The apparatus of claim 18, further comprising a storing and delivery station,
    said storing and delivering station being arranged between said erecting station and said transfer unit,
    said storing and delivery station being designed and arranged to accumulate the lines of tablets and to deliver the tablets into said impressions of said transfer unit corresponding to the arrangement of the pockets in the bottom foil.

21. The apparatus of claim 11, further comprising a control station,
    said control station being designed and arranged to check the tablets with respect to damages and to cause removal of damaged tablets.

22. The apparatus of claim 16, further comprising a unit for sucking off pieces and dust of tablets from in between said lamellas.

23. The apparatus of claim 16, further comprising a unit for sucking off pieces and dust of tablets from said impressions and said channels.

* * * * *